(12) United States Patent
Gunnsteinsson et al.

(10) Patent No.: US 12,611,324 B2
(45) Date of Patent: Apr. 28, 2026

(54) ORTHOPEDIC WALKER

(71) Applicant: Ossur Iceland ehf, Reykjavik (IS)

(72) Inventors: Larus Gunnsteinsson, Reykjavik (IS);
Tomas Njalsson, Reykjavik (IS)

(73) Assignee: OSSUR ICELAND EHF, Reykjavik
(IS)

( * ) Notice: Subject to any disclaimer, the term of this
patent is extended or adjusted under 35
U.S.C. 154(b) by 298 days.

(21) Appl. No.: 18/459,862

(22) Filed: Sep. 1, 2023

(65) Prior Publication Data

US 2024/0074886 A1     Mar. 7, 2024

Related U.S. Application Data

(60) Provisional application No. 63/403,492, filed on Sep.
2, 2022.

(51) Int. Cl.
*A61F 5/01*          (2006.01)

(52) U.S. Cl.
CPC .......... *A61F 5/0195* (2013.01); *A61F 5/0111*
(2013.01)

(58) Field of Classification Search
CPC .... A61F 5/0111; A61F 5/0127; A61F 5/0195;
A43B 7/18; A43B 7/20
See application file for complete search history.

(56) References Cited

U.S. PATENT DOCUMENTS

| | | | |
|---|---|---|---|
| 1,639,381 A | 8/1927 | Manelas | |
| 3,878,626 A | 4/1975 | Isman | |

| | | | |
|---|---|---|---|
| 4,267,650 A | 5/1981 | Bauer | |
| 4,376,438 A | 3/1983 | Straube et al. | |
| 4,771,768 A | 9/1988 | Crispin | |
| 4,974,583 A | 12/1990 | Freitas | |
| 5,078,128 A | 1/1992 | Grim et al. | |
| 5,250,021 A | 10/1993 | Chang | |
| 5,329,705 A | 7/1994 | Grim et al. | |
| 5,355,562 A | 10/1994 | Matoba et al. | |
| 5,368,551 A | 11/1994 | Zuckerman | |
| 5,452,527 A | 9/1995 | Gaylord | |
| 5,464,385 A | 11/1995 | Grim | |
| 5,546,642 A | 8/1996 | Anscher | |
| 5,713,837 A | 2/1998 | Grim et al. | |
| 5,716,335 A | 2/1998 | Iglesias et al. | |
| 5,983,528 A | 11/1999 | Hartung | |
| 6,102,881 A | 8/2000 | Quackenbush et al. | |
| D634,852 S | 3/2011 | Hu | |
| 7,896,826 B2 | 3/2011 | Hu et al. | |

(Continued)

FOREIGN PATENT DOCUMENTS

| | | |
|---|---|---|
| AU | 2020274308 B2 | 11/2020 |
| CN | 105361990 A | 3/2016 |

(Continued)

OTHER PUBLICATIONS

International Search Report from Corresponding PCT Application
No. PCT/US2023/031837, Dec. 15, 2023.

*Primary Examiner* — Keri J Nelson
(74) *Attorney, Agent, or Firm* — Workman Nydegger

(57)          ABSTRACT

An orthopedic walker includes an outsole and a base. The
outsole is formed from a thermoplastic elastomer and has
protrusions or recesses interlocking corresponding protru-
sions or recesses of the base. The outsole is securely attached
in place to the base due to a shrink-fit about at least a portion
of the base and without adhesive.

15 Claims, 7 Drawing Sheets

(56)  References Cited

U.S. PATENT DOCUMENTS

| | | | |
|---|---|---|---|
| 8,021,316 | B2 | 9/2011 | Franke et al. |
| 8,043,245 | B2 | 10/2011 | Campos et al. |
| 8,192,434 | B2 | 6/2012 | Huebner et al. |
| 8,403,872 | B2 | 3/2013 | Franke et al. |
| 8,409,123 | B2 | 4/2013 | Hoffmeier et al. |
| 8,540,655 | B2 | 9/2013 | Franke et al. |
| 8,672,865 | B2 | 3/2014 | Franke et al. |
| D729,393 | S | 5/2015 | Dunn et al. |
| D742,017 | S | 10/2015 | Dunn et al. |
| D744,111 | S | 11/2015 | Dunn et al. |
| 9,180,038 | B2 | 11/2015 | Ingimundarson et al. |
| 9,248,042 | B2 | 2/2016 | Lopez et al. |
| 9,271,860 | B2 | 3/2016 | Romo |
| 9,492,305 | B2 | 11/2016 | Hecker et al. |
| 9,510,965 | B2 | 12/2016 | Grim et al. |
| 9,668,907 | B2 | 6/2017 | Romo et al. |
| 9,744,065 | B2 | 8/2017 | Walborn et al. |
| 9,839,548 | B2 | 12/2017 | Ingvarsson et al. |
| 9,839,549 | B2 | 12/2017 | Walborn et al. |
| D813,089 | S | 3/2018 | Frost et al. |
| 9,925,082 | B2 | 3/2018 | Chetlapalli et al. |
| 10,039,664 | B2 | 8/2018 | Grim et al. |
| D835,289 | S | 12/2018 | Frost et al. |
| D846,130 | S | 4/2019 | Watabe et al. |
| 10,391,211 | B2 | 8/2019 | Walborn et al. |
| 10,449,078 | B2 | 10/2019 | Grim et al. |
| 10,561,514 | B2 | 2/2020 | Romo et al. |
| 10,863,791 | B2 | 12/2020 | Iglesias et al. |
| 11,096,816 | B2 | 8/2021 | Abdul-Hafiz et al. |
| 11,253,383 | B2 | 2/2022 | Hanft |
| D958,379 | S | 7/2022 | Hanft |
| 2009/0306565 | A1 | 12/2009 | Chan |
| 2013/0267878 | A1 | 10/2013 | Franke et al. |
| 2014/0265018 | A1 | 9/2014 | Grim et al. |
| 2014/0296762 | A1* | 10/2014 | Hecker ................. A61F 5/0585 602/28 |
| 2015/0088046 | A1* | 3/2015 | Walborn ............... A61F 5/0195 602/27 |
| 2015/0208760 | A1 | 7/2015 | Chen |
| 2016/0015121 | A1 | 1/2016 | Romo et al. |
| 2016/0045354 | A1 | 2/2016 | Lee et al. |
| 2016/0302957 | A1* | 10/2016 | Iglesias ................ A43B 13/188 |
| 2019/0240057 | A1 | 8/2019 | Gunnsteinsson et al. |
| 2022/0151812 | A1 | 5/2022 | Gunnsteinsson et al. |
| 2022/0183869 | A1 | 6/2022 | Morris |

FOREIGN PATENT DOCUMENTS

| | | | |
|---|---|---|---|
| CN | 111801071 | A | 10/2020 |
| CN | 114173601 | A | 3/2022 |
| DE | 2651089 | A1 | 5/1978 |
| EP | 1227774 | B1 | 9/2003 |
| EP | 2249756 | B1 | 7/2015 |
| EP | 3034051 | B1 | 8/2018 |
| EP | 2967961 | B1 | 2/2019 |
| EP | 3294233 | B1 | 3/2019 |
| EP | 3474697 | B1 | 3/2020 |
| EP | 3476373 | B1 | 11/2021 |
| EP | 3801402 | B1 | 7/2023 |
| TW | I538666 | B | 6/2016 |
| WO | 2008100487 | A2 | 8/2008 |
| WO | 2008133970 | A1 | 11/2008 |
| WO | 2012063049 | A2 | 5/2012 |
| WO | 2015042214 | A1 | 3/2015 |
| WO | 2015089261 | A1 | 6/2015 |
| WO | 2023287689 | A1 | 1/2023 |

* cited by examiner

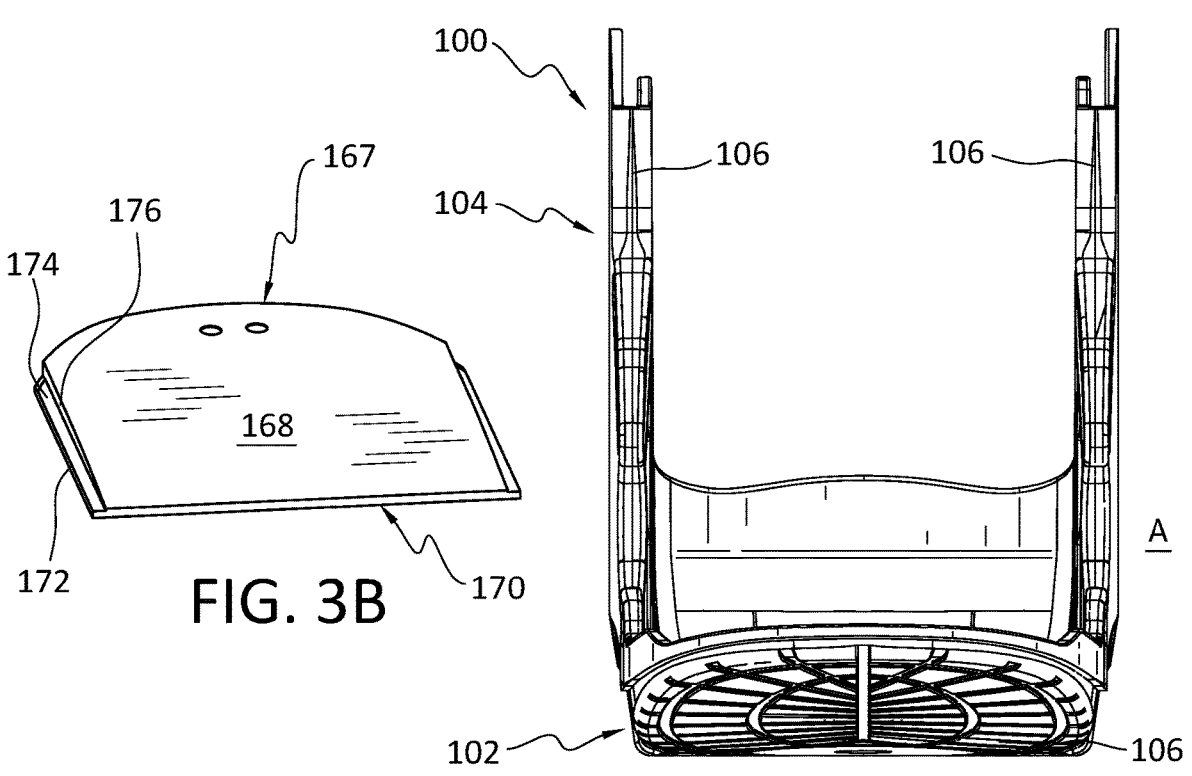
FIG. 3B
FIG. 4
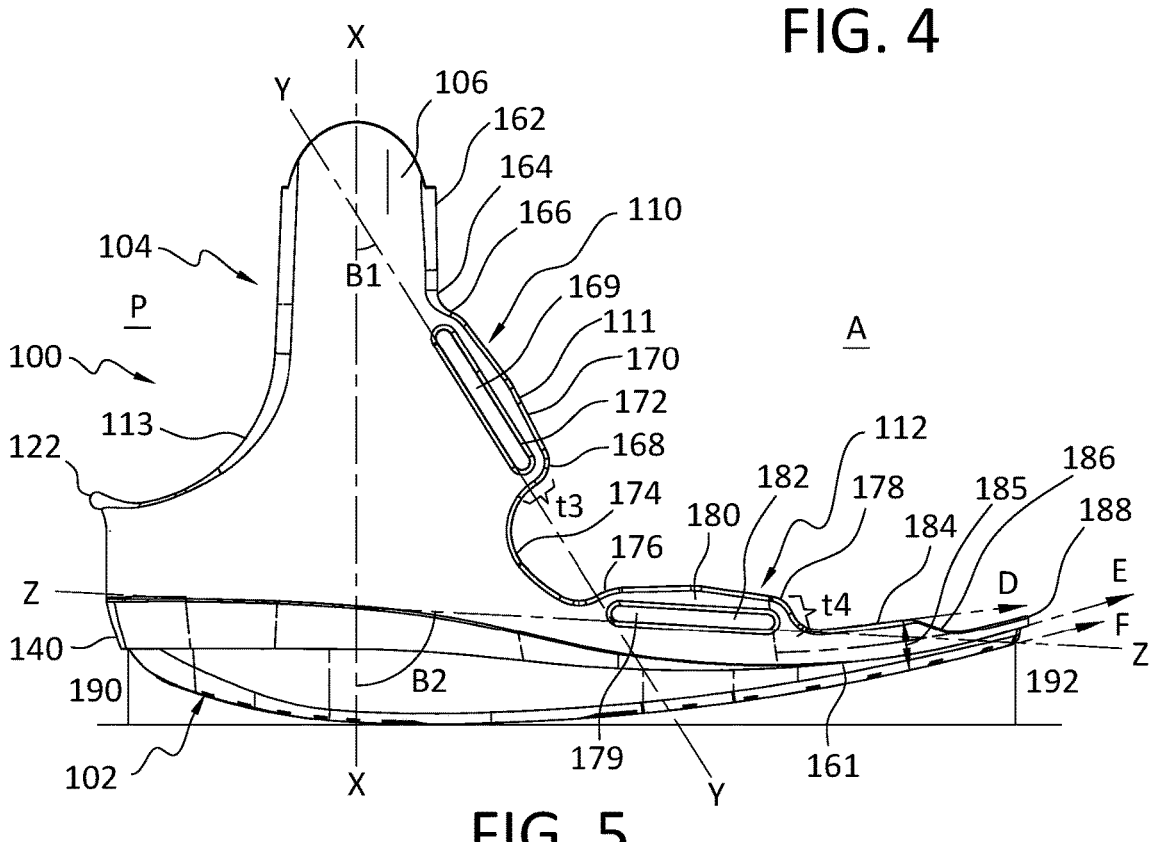
FIG. 5

ORTHOPEDIC WALKER

FIELD OF THE DISCLOSURE

This disclosure relates to orthopedic walkers, which are orthopedic support boots that encompass the foot, ankle, and lower leg for use by persons recovering from injuries such as broken bones or other trauma of the lower leg, ankle, or foot.

BACKGROUND

One of the main purposes of orthopedic leg mounted walkers, or walking boots (collectively referred to herein as "walkers"), is to provide immobilization to the lower leg, in particular the foot and ankle, as well as to provide compression to the lower leg post fracture, sprain, or another injury, such as Achilles tendon rupture. An example of an orthopedic leg-mounted walker is in U.S. Pat. No. 7,896,826, granted Mar. 1, 2011, and incorporated herein by reference.

To maximize its effect and provide comfortable wear to the user of the walker, it is desirable that a walker securely and precisely fits the leg of the wearer. While walkers generally conform to the geometry of the leg of a wearer, it is common for the geometry of the leg to change during the healing and treatment process. The geometry requires the walker to ideally accommodate a variety of contours and geometries of the leg.

A common feature with many conventional walkers is a pair of struts formed from a high-strength material used as a frame upon which circumferential straps are secured. A soft-good support is wrapped around the leg, foot, and ankle and contained within the struts. The straps are typically secured to the struts via corresponding hook and loop fastening material. Separate or distinct D-rings further accompany them to allow tensioning of the straps relative to the struts.

The normal operation of the foot provides a smooth rolling motion through a step when ambulating. In a normal gait, the load on a person's foot moves from heel to toe at an angle from the lateral side or outside of the foot (supination) to the medial side or inside of the foot (pronation). A normal step begins with the heel strike as the heel is set down on the support surface or ground and ends with the toe-off as the large toe pushes the foot off the support surface.

Over the years, many efforts have been made to construct an outsole for orthopedic devices that promotes a healthy and natural gait. One such outsole construction is tapered or curved directly from back to front in a linear fashion. Such a design initiates a rollover, limited to straight ahead from back to front, allowing heel strike, rocking straight forward, then toe-off. However, most people do not walk with their feet pointed straight ahead. Rather, most people walk with their feet externally rotated. When feet point outward, it is commonly called toed-out or exorotated. When feet point inward, it is commonly called toed-in, a tendency referred to as walking "pigeon-toed."

Because people do not walk with their feet straight forward, the linear rollover motion of known outsoles resists the natural gait of the wearer's foot, adding stress and discomfort to the wearer as the wearer ambulates. This dynamic can adversely affect recovery and cause undesirable biomechanical compensations, which can cause problems for the wearer in the long term. Such problems include but are not limited to bad posture, back problems, an unhealthy gait, foot abnormalities, muscle imbalances in the foot and leg, and pressure ulcers.

The linear rollover motion of known outsoles also causes foot and leg fatigue because the outsole's action conflicts with the user's natural rollover motion, requiring the user to adjust or correct the position of the user's foot while walking. It also can create awkward pressure points on the user's lower leg and foot due to the orthopedic device being urged unnaturally against the user's lower leg and foot while walking.

There exists a need for improved outsoles for orthopedic devices that facilitate a more natural and comfortable rollover motion of a user's foot from heel strike through toe-off.

Considering the needs above in orthopedic walkers, healthcare providers in the United States and the rest of the world are trying to respond to the tremendous pressure to reduce costs. While there is a cost burden, there is a desire to avoid compromising the performance of the orthopedic walker. Indeed, there is a need to provide an orthopedic walker that provides superior performance over existing commercial walkers while simplifying manufacturing and streamlining features to balance the challenge of cost burden.

SUMMARY

An orthopedic walker or walking boot is arranged with a construction for facilitating donning and doffing, providing a limb with reliable protection and support. In exemplary embodiments, the orthopedic device described herein may be a lightweight walker. It is also contemplated that other orthopedic devices may utilize similar configurations as described below.

The disclosure describes various embodiments of an outsole for an orthopedic device, providing construction and design that facilitates a more natural rollover motion of the user's foot from heel strike through toe-off. The heel thickness of the walker is reduced, compared to conventional orthopedic walkers, so that the outsole more closely matches the heel height of an unimpaired foot of a user relative to the ground. The heel thickness is at least achieved by modifying the lattice structure of the heel, such as by modifying the thicknesses of the various ribs forming the lattice structure.

The orthopedic walker comprises a base and an overmolded outsole integrated with the base. The overmolded outsole does not require adhesive or glue to connect to the walker's base. Indeed, by the design of the base and the overmolded outsole, the orthopedic walker is devoid of an adhesive or glue, and rather the outsole, constructed from a rubber-like plastic (i.e., thermoplastic elastomer), is molded over the base formed from a structural plastic part, that may be reinforced with glass or composite fiber. The overmolded outsole reduces manufacturing costs and improves the connection between the outsole and the base of the walker.

The base features a textured surface, recessed grooves, and a groove proximate to the peripheral edge of the base to avoid detachment of the outsole from the side of the base. The walker's base removes the need for separate D-ring components and features integrated, molded slots to receive straps and fasteners. The molded slots reduce the overall profile of the walker and introduce a simplified design compared to traditional and complex multi-component walkers and fastening systems. The walker's base also features ribs that taper in width toward a median plane of the walker so that the base can be easily demolded from lifter inserts. Additional features and advantages of embodiments of the present disclosure will be outlined in the following description and will be obvious from the description or may be learned by the practice of such exemplary embodiments. These and other features will become more apparent from the following description or may be learned by the practice of such exemplary embodiments as set forth from now on.

Glossary

A description of a few terms is necessary to understand the embodiments of an orthopedic device as disclosed herein. As used herein, the term "dorsal" has its ordinary meaning and refers to the top surfaces of the foot, ankle, and foreleg or shin. As used herein, the term "plantar" has its ordinary meaning and refers to a bottom surface, such as the bottom of a foot. As used herein, the term "proximal" has its ordinary meaning and refers to a location closer to the heart than another. Likewise, the term "distal" has its ordinary meaning and refers to a location that is further from the heart than another location. The term "posterior" also has its ordinary meaning and refers to a location behind or the rear of another location. Lastly, the term "anterior" has its ordinary meaning and refers to a location that is ahead of or to the front of another location.

A frontal or coronal plane, Fp, defines the anterior and posterior portions as depicted in FIG. 2. The anterior and posterior portions of the orthopedic walker function together to support and stabilize the lower limb of a user.

The term "lateral" has its ordinary meaning and refers to a location away from the midline of a user's body. The term "medial" also has its ordinary meaning and refers to a location closer to or toward the midline of a user's body. The lateral and medial portions of the walker are defined by a median or sagittal plane, Mp, as depicted in FIG. 2. The lateral and medial portions of the orthopedic walker function together to support and stabilize the lower limb of a user. As shown in at least FIG. 2, when the orthopedic walker is universal or generally symmetric for both right and left legs and feet, the first and second sides of the orthopedic walker SI, SII, are divided by the median plane.

The terms "rigid," "flexible," and "resilient" may be used herein to distinguish characteristics of portions of certain features of the orthopedic device. The term "rigid" denotes that an element of the device is generally devoid of flexibility. Within the context of support members or shells that are "rigid," it is intended to indicate that they do not lose their overall shape when force is applied and that they may break if bent with sufficient force. On the other hand, the term "flexible" is intended to denote that features are capable of repeated bending such that the features may be bent into retained shapes or that features do not retain a general shape but continuously deform when force is applied. The term "resilient" qualifies such flexible features as returning to an initial general shape without permanent deformation. The term "semi-rigid" connotes the properties of support members or shells that provide support and are free-standing; however, such support members or shells may have some degree of flexibility or resiliency.

The term "user" refers to a person who uses an orthopedic device. The user may be a patient or an operator. The term "clinician" refers to a clinical specialist, supervisor, therapist, doctor, or person with a similar role that assists or oversees the operation of the exoskeleton by the user.

The term "generally" connotes near or almost, and in a range of 90% or more than what is "generally" compared to.

The term "interlock" means two or more parts that engage with each other by overlapping or fitting together with projections and recesses.

The term "plurality" connotes two or more of a given element or feature.

The term "outer" means the element is further away from the user's body. Likewise, the term "inner" means close or proximate to the user's body.

The term "bearing surface" has its ordinary meaning and refers to the contact area between two elements.

The term "protrusion" or "post" has its ordinary meaning and refers to an element extending from a surface.

The term "peripheral" has its ordinary meaning and refers to an element's edge or surrounding surface.

The term "clearance" refers to the space, distance, or allowance between elements.

The term "unitary form construction" means differently formed sections molded simultaneously or post-fabricated with at least another differently formed section.

The term "overmold" or overmolding means an injection molding process used to mold one plastic (commonly a rubber-like plastic called "thermoplastic elastomer" or TPE) over top of another component (substrate).

A TPE is commonly understood as being selected from a class of copolymers or a physical mix of polymers (usually a plastic and a rubber) that consist of materials with both thermoplastic and elastomeric properties. While most elastomers are thermosets, thermoplastics are, in contrast, relatively easy to use in manufacturing, for example, by injection molding. Thermoplastic elastomers have advantages typical of both rubbery materials and plastic materials. The benefit of using thermoplastic elastomers is the ability to stretch to moderate elongations and return to their near-original shape, creating a longer life and better physical range than other materials.

The term "shrinkage rate" requires that a plastic material is heated and cools as it is molded, and that materials expand when heated and shrink as they cools to room temperature. The dimensions of the plastic product will shrink a certain amount during its cooling period, defined as the shrinkage rate. The expression "shrink-fit" indicates the shrinkage of plastic over another structure to form an interference fit by a relative size change after assembly (i.e., the outsole is initially hot and cools to form a shrink-fit over the base).

The term "filled polymer" connotes a moldable composite material that includes a filler, such as reinforcement fibers or microspheres or other filler materials, in a matrix of polymer material.

It will be understood that unless a term is defined to possess a described meaning, there is no intent to limit the meaning of such term, either expressly or indirectly, beyond its plain or ordinary meaning. The embodiments of the disclosure are adapted for a human body and may be dimensioned to accommodate different types, shapes, and sizes of human body sizes and contours.

BRIEF DESCRIPTION OF THE DRAWINGS

The drawing figures are not necessarily drawn to scale but instead are drawn to provide a better understanding of the components thereof and are not intended to be limiting in scope but to provide exemplary illustrations. The figures illustrate exemplary configurations of an orthopedic device and in no way limit the structures or configurations of an orthopedic walker according to the present disclosure.

FIG. 3B is a perspective view of a heel plate shown schematically in the walker of FIG. 3A.

FIG. 4 is a front plane view of the walker in FIG. 1.

FIG. 5 is a side plane view of the walker in FIG. 1.

Figure 1:
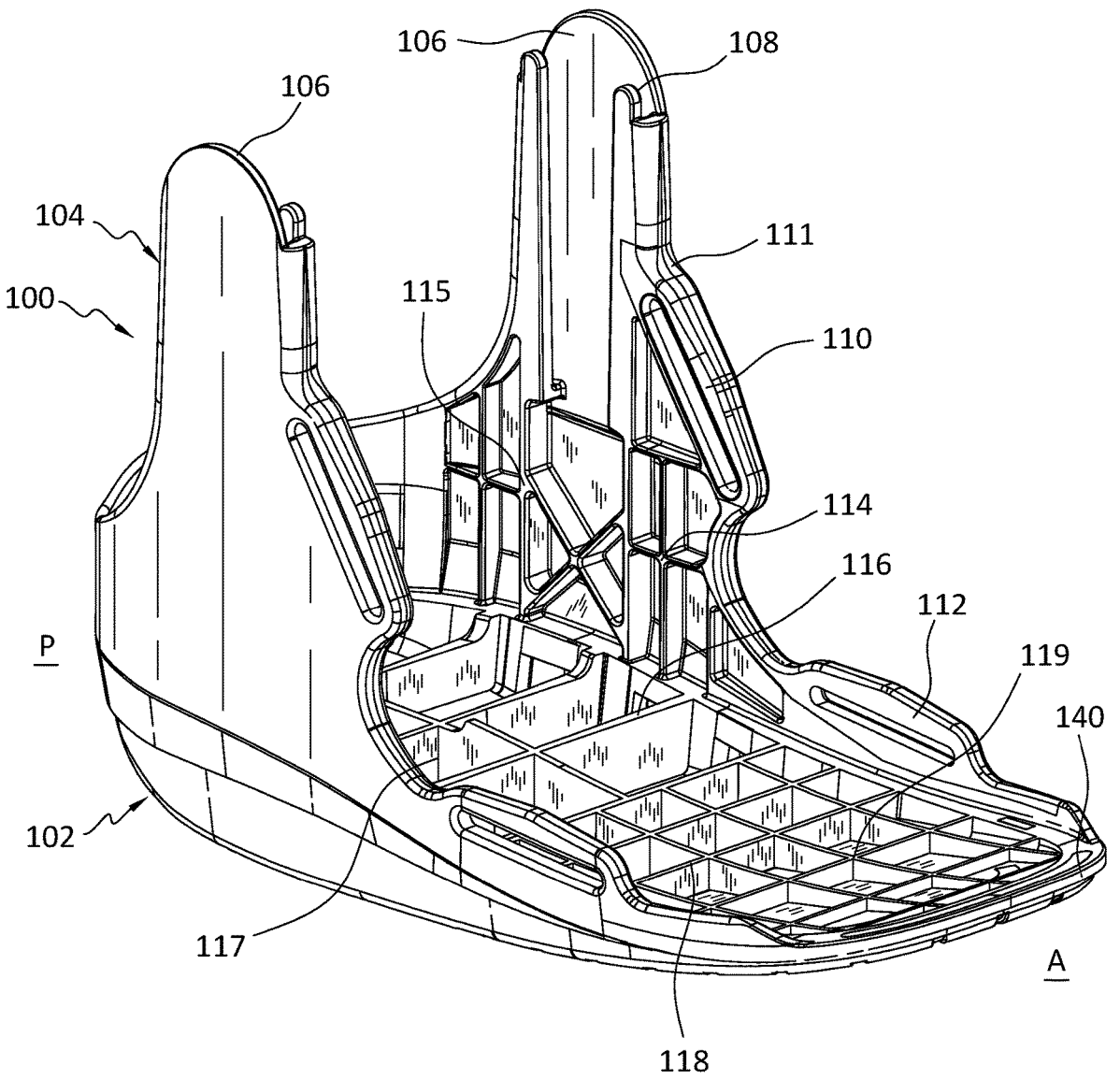
FIG. 1 is a perspective view of an embodiment of an orthopedic walker comprising an outsole and a base.

While the disclosure is susceptible to various modifications and alternative constructions, certain illustrative embodiments are in the drawings and are described below. It should be understood, however, that there is no intention to limit the disclosure to the specific embodiments disclosed. On the contrary, the intent is to cover all modifications, alternative constructions, combinations, and equivalents falling within the spirit and scope of the disclosure.

Prior Art Orthopedic Walker

Figure 1A:
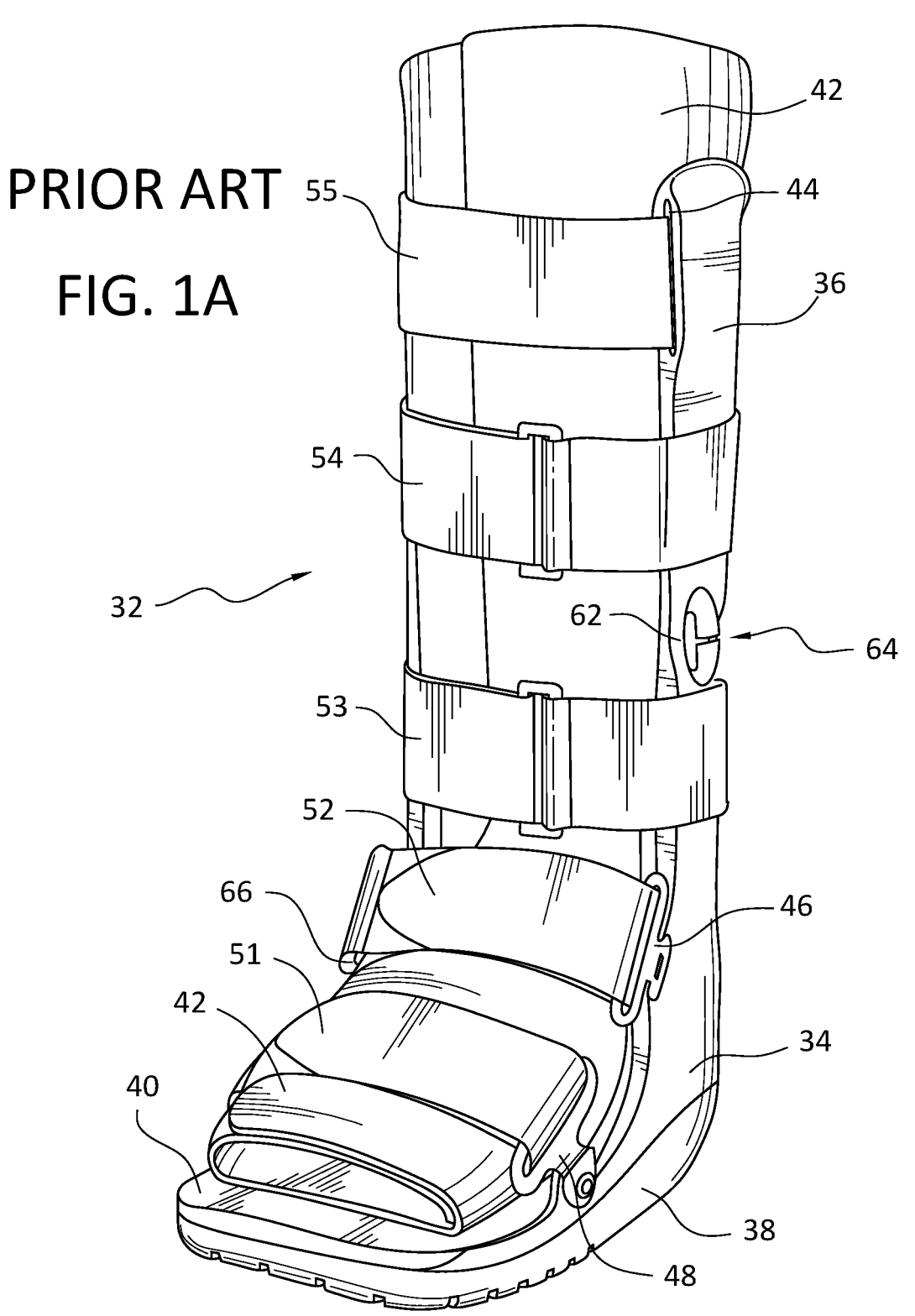
FIG. 1A is a perspective view of a prior art embodiment of an orthopedic walker.

Referring to the drawings, FIG. 1A is a perspective view of a known orthopedic walker 32 found in U.S. Pat. No. 7,896,826. FIG. 1A includes an engineered plastic base 34, two struts visible at reference 36, and an outer sole or outsole 38. For example, the plastic base 34 may be formed from a structural plastic such as a fiber-filled polymer (such as nylon), but other high-strength plastics or other materials, such as aluminum, may be powder coated. A resilient layer or insole 40, which may be formed of a one-quarter-inch thick resilient foam, provides a cushion between the foot and the upper surface of the plastic base 34.

Additional padding 42 extends around the patient's foot, ankle, and lower leg. The padding 42 is held in place between the struts, including strut 36, by hook and loop material of the VELCRO type, with hook type material extending along the inner surface of the struts, and with the padding 42 either having mating loop material on its outer surface or being of a type of fabric which will inherently mate with hook type material.

The straps 51 through 55 extend around the padded foot, ankle, and lower leg of the patient. They are secured to the base 34 and the struts by slots, such as slot 44 in strut 36 or by b-rings, such as D-ring 46 or pivoted D-ring 48. The straps have mating hook and loop material on their overlapping surfaces to be readily adjustable.

DETAILED DESCRIPTION OF VARIOUS EMBODIMENTS

A better understanding of the disclosure may be had from the following description read with the accompanying drawings, which, like reference characters, refer to like elements.

While the disclosure is susceptible to various modifications and alternative constructions, certain illustrative embodiments are described in the drawings below. It should be understood, however, that there is no intention to limit the disclosure to the embodiments disclosed. On the contrary, the intention covers all modifications, alternative constructions, combinations, and equivalents falling within the spirit and scope of the disclosure.

FIG. 1 shows a perspective view of an orthopedic walker 100. The orthopedic walker has an outsole 102 and a base 104 formed by a unitary form construction. The base 104 is preferably formed from a single material and arranged to receive the lower leg of a user. The term "unitary form construction" indicates that differently formed sections, such as the outsole 102 and the base 104, have been molded simultaneously or post-fabricated with at least another differently formed section. The base 104 consists of a single material part with various features supporting extraneous features.

The extraneous features to the unitary form construction of the base 104 may include fasteners or straps, which may be connected to molded slots 110, 112, or additional supports inserted into the notch 108 on the strut supports 106, such as a strut, rod, or bar forming part of a framework to stabilize the lower leg of the user. As discussed in greater detail in FIG. 5, the molded slots 110 and 112 are formed and arranged within the anterior periphery 111 of the base 104.

The molded slots 110 and 112 allow for a reduced base profile. The molded slots 110, and 112 also reduce manufacturing costs by removing the added complexity of distinct D-ring elements. In one embodiment, additional molded slots may be formed and arranged within the posterior periphery 113 of the base 104. The strut supports 106 may extend upward from the base 104 and along the user's lower leg to stabilize the user's lower leg. The strut supports 106 may receive detachable struts within the notch 108 of variable sizes to accommodate the anatomy of different users.

The base 104 has a shape corresponding to a lower limb of a user and a unitary form construction to fit against the lower limb intimately. The base 104 is configured to receive a lower limb of a user and may be configured to an intended treatment purpose for the user. The height of the base 104 may vary depending on the condition to be treated. The base 104 may have a high top extending up the user's lower leg or be manufactured or trimmed to have a low top. The orthopedic walker 100 may be configured at different heights to accommodate the pathologies and indications used for treatment.

The base 104 may be formed as a single part from a rigid or semi-rigid material. The rigid or semi-rigid material reduces the complexity, cost, and weight of the orthopedic walker 100. The rigid or semi-rigid nature of the material provides rigid support to the limb. It allows the orthopedic walker 100 to hold or return to the original shape while having flexibility or resiliency to facilitate regular donning and doffing. Preferred materials for forming the base 104 include a structural plastic such as a filled polymer, such as fiber-filled nylon, but other high-strength plastics or other materials an expanded polymer, or materials such as EVA (ethylene vinyl acetate), rubber foam, or closed-cell foam. Alternate polymeric materials may be employed, having enough rigidity to intimately support and hold the lower limb and foot while offering a protective barrier to elements. The materials for forming the base 104 may also advantageously reduce the weight of the orthopedic walker 100 without sacrificing the needed robustness.

The rigid or semi-rigid base material may be configured to have distinct material properties, including material thickness, densities, etc., according to a preferred treatment and stabilization. In some embodiments, the rigid or semi-rigid base material may be configured such that the base 104 provides compression for securing the base 104 about the limb when no force or pressure is applied to the base 104.

A shape of the base 104 may be configured to support a particular area or prevent a particular limb's particular motion.

The base 104 comprises strut supports 106, the heel support 116, and the toe support 118. The strut supports 106 comprise reinforcements 114 to prevent or restrict lower limb movement. The strut supports 106 feature a strut lattice structure 115 extending upward from the heel support 116 and providing additional structural support to the strut supports 106. The strut lattice structure 115 reduces material costs and reinforces the base 104 at predefined positions along the lower limb of a user.

The heel support 116 features a heel lattice structure 117 arranged between the posterior end of the base 104 and the toe support 118. The heel lattice structure 117 reduces material costs and reinforces the base 104 to support the heel and foot of the user. The toe support 118 features a toe lattice structure 119 arranged between the heel support 116 and the anterior end of the base 104. The toe lattice structure 119 reduces material costs and reinforces the base 104 to support the toes and feet of the user.

Figure 2:
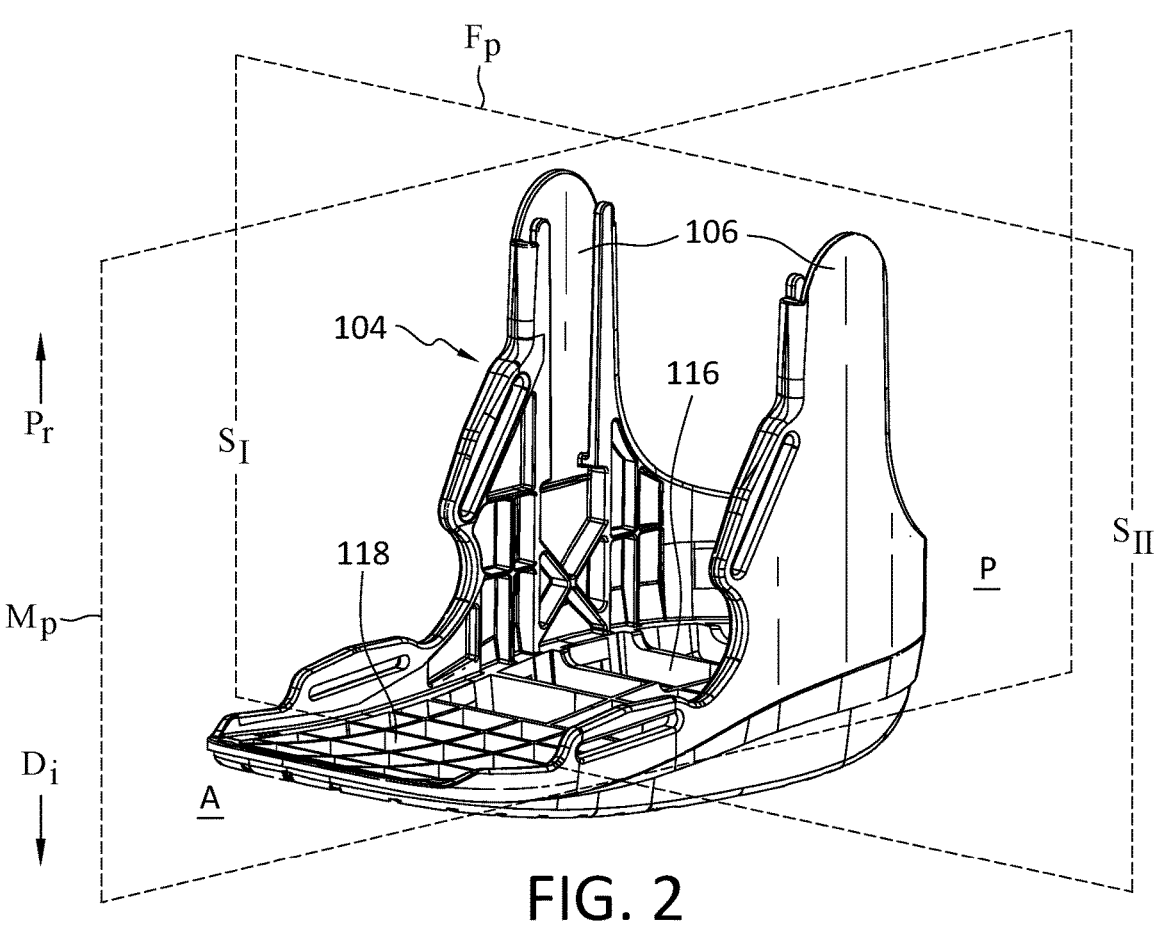
FIG. 2 is a perspective view of an embodiment of the orthopedic walker base in FIG. 1.

FIG. 2 shows a perspective view of the base 104 in FIG. 1. The anterior A and posterior P portions of the walker 100 are defined by a frontal plane Fp. When the orthopedic walker is universal or generally symmetric for both right and left legs and feet, the first and second sides of the orthopedic walker SI, SII, are divided by the median plane Mp.

Figure 3A:
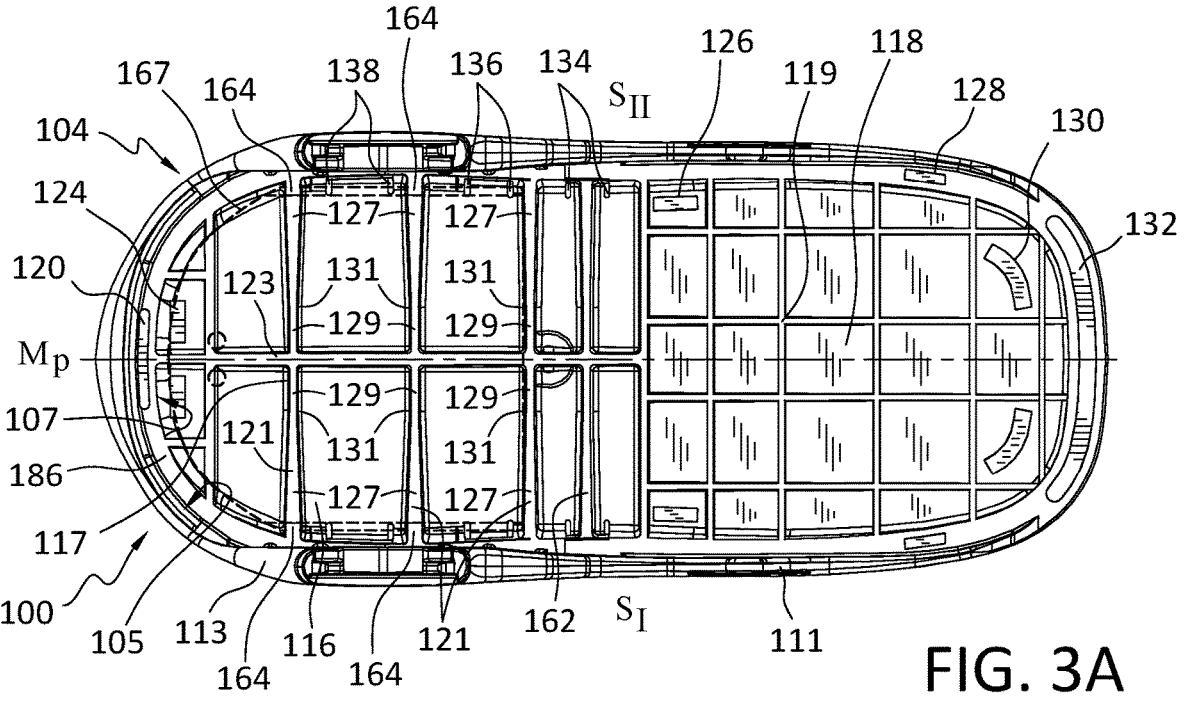
FIG. 3A is a top plane view of the base of the walker in FIG. 1.

FIG. 3A shows a top plane view of the walker 100 in FIG. 1. The heel lattice structure 117 features at least one rib 121 that extends between the first and second sides SI, SII of the walker 100. At least one rib 121 is generally parallel to the frontal plane Fp and generally perpendicular to the median plane Mp. The heel lattice structure 117 features at least one medial rib 123 arranged along the median plane Mp and positioned between the posterior P portion of the walker and the toe support 118. The at least one rib 121 preferably tapers in thickness from the first and second sides SI, SII toward the median plane Mp. This arrangement allows the heel lattice structure 117 to be easily demolded from lifter inserts.

The at least one rib 121 preferably has a tapered thickness extending away (toward the inner periphery of the base) from the at least one medial rib 123, with a greatest thickness 127 toward an inner cavity 107 and from the smallest thickness 129 near or at the at least one medial rib 123. The tapering section 131 may be inconsistent in that at a certain point the thickness remains at the greatest thickness 127 or the smallest thickness for a sustained length of the at least one rib 121. The at least one medial rib 123 may have a thickness greater than the smallest thickness 129 of the at least one rib 121; however the greatest thickness 127 may be greater than the thickness of the at least one rib 121. The enhanced thickness of the medial rib 123 provides greater stability for the base and the greatest thickness of the at least one rib toward the inner periphery of the base.

FIGS. 3A and 3B illustrate that a heel plate 167 may be inserted at the heel portion of the base to cover the at least one rib and the at least one medial rib to create enhanced comfort in addition to the insole 40 in FIG. 1. An insole therefore can or is provided in the base, as in FIG. 1, although for simplicity reference is made to FIG. 1 and the insole is not shown in FIG. 3A. To secure the heel plate 167, seat tabs 165 are defined along the inner periphery 105 of the base so that the heel plate can sit in register to the seat tabs 165 and below inner contour 186 (see also FIG. 10) of the base and along which the insole extends. The seat tabs 165 retain the heel plate in place, and the compressibility of the foam may be used to wedge the heel plate underneath the seat tabs 165 effectively. Therefore, the heel plate 167 rests in a recessed portion of the base, locked in by the seat tabs 165, so as not to interfere with the insole but rather to supplement the insole by adding more cushion to a user's heel.

FIG. 3B illustrates an embodiment of the heel plate 167. The heel plate 167 defines an outer periphery 172 having a ledge portion 174, with an inner edge 176 defined inward, permitting the ledge 174 to rest and correspond to the seat tabs 165. The ledge 174 is arranged to secure under the seat tabs 165, and generally within the inner cavity 107 of the base 104, and just to the inner contour 186. Hence, the insole extends over the outer surface 168 of the heel plate 167 without interruption. The inner surface 170 of the heel plate 167 rests upon the aforementioned ribs in the inner cavity 107. The heel plate 167 may be formed from foam, a TPE or other appropriate cushioning material.

Figure 8:
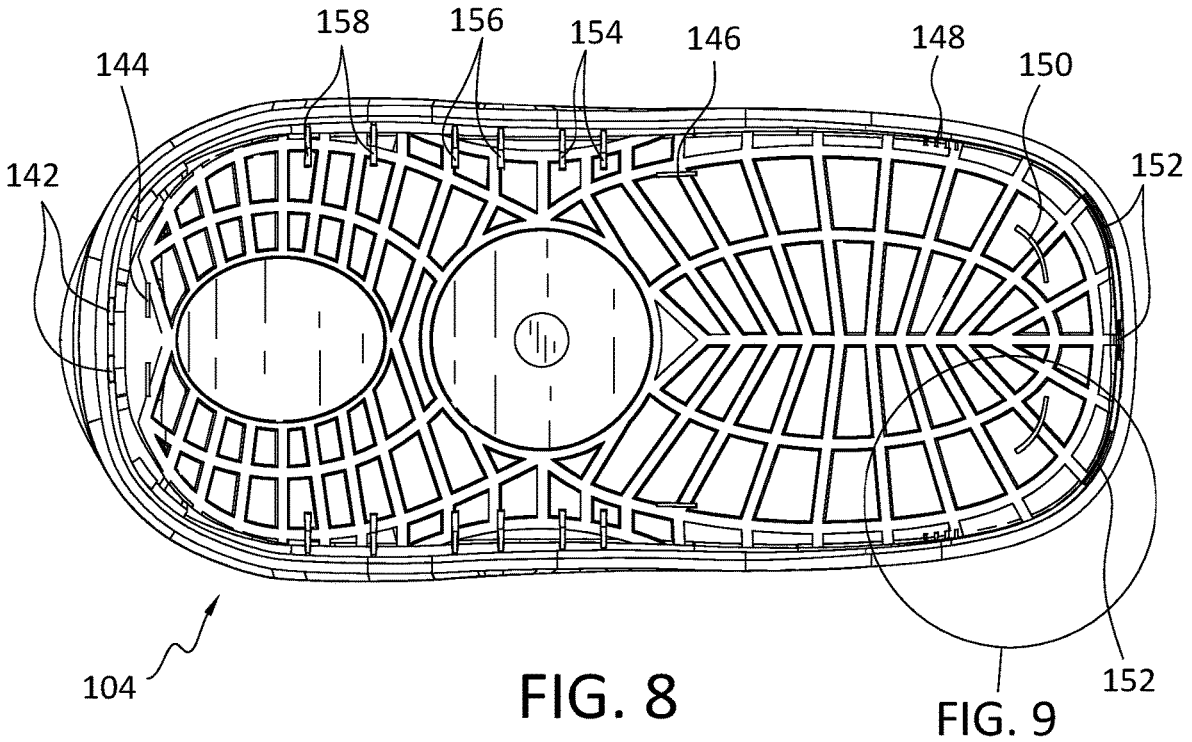
FIG. 8 is a bottom plan view of the walker of FIG. 1.

The outsole 102 features attachment posts 120, 124, 126, 128, 130, 132, 134, 136, and 138, or protrusions, that connect to the base 104 through openings 142, 144, 146, 148, 150, 152, 154, 156, 158, or apertures, as observed in FIG. 8. The overmold of the outsole 102 allows for an integrated connection between the outsole 102 and base 104. Attachment posts 126, front edge attachment posts 128, inner toe attachment posts 130, outer toe attachment post 132, front side post 134, middle side post 136, and back side post 138 reinforce the connection between the outsole 102 and the base 104 and do not require the use of adhesives and glue.

FIG. 4 provides another example of the thickness variability of the outsole 102. A tread 160 of the outsole 102 of the orthopedic walker 100 may be configured with a pattern and texture to prevent slippage and lead to smooth rollover during walking with the orthopedic walker donned.

FIG. 5 shows a side view of the base 104, and the outsole 102 of the walker at the anterior periphery 111 of the base 104 forms a transition 164 between the strut edge 162 and the first side 166 of the molded slot 110 to an outer periphery 170 of the molded slot 110. The transition 164 allows for a reduced profile of the walker 100 and prevents the walker 100 from getting caught on clothing and other materials. The anterior periphery 111 also forms a transition periphery 174 between a second side 168 of the molded slot 110 and a first side 176 of the molded lower slot 112 to an outer periphery 180 of the molded lower slot 112. The transition periphery 174 also reduces the profile of the walker 100. The anterior periphery 111 of the base 104 forms a transition 186 at a toe end 188. The transition 186 reduces the profile of the walker 100 and provides greater flexibility to the toe support 118 of the base 104. The transitions 164, 186, and transition periphery 174 also facilitate an improved gait of the user.

The molded slot 110 comprises an opening 172 that extends between the first and second sides 166, and 168 of the molded slot 110 and forms an inner periphery 169 adjacent to the anterior periphery 111 of the base 104. The molded lower slot 112 also comprises an opening 182 that extends between the first and second sides 176, 178 of the molded lower slot 112 and forms an inner periphery 179 adjacent to the anterior periphery 111 of the base 104. The openings 172, and 182 of the molded slots 110, and 112 reduce manufacturing costs by removing the added complexity of distinct D-ring elements and may interface with different straps and fasteners to secure the lower limb of a user within the walker 100. In a preferred embodiment, the molded slots 110, and 112 are elongated in shape. The molded slots 110, and 112 may vary in thickness t3, and t4 to accommodate the different straps and fasteners.

The inner periphery 169 of the molded slot 110 extends along axis Y. The offset angle B1 is determined between axis Y and axis X, axis X being substantially vertical or substantially perpendicular to the ground (e.g., approximately 88 degrees). The inner periphery 179 of the molded lower slot 112 extends along axis Z, wherein the offset angle B2 is determined between axis Z and axis X. Offset angle B1 is preferably between 30 and 60 degrees, and offset angle B2 is preferably between 60 and 90 degrees.

The base 104 and the outsole 102 curve upward toward anterior A and posterior P portions of the walker 100. The base 104 forms a surface trajectory 184 between the second side 178 of the molded lower slot 112 and the transition 186 at the toe end 188. The surface trajectory 184 follows a trajectory D, a first trajectory D. The borderline 161 between the base 104 and the outsole 102 follows a second trajectory E. The distal end Di of the outsole 102 follows a third trajectory, F. The variance 185 in trajectories D, E, and F allows for greater flexibility at the toe end 188 and improves the rollover of the walker 100. In an embodiment, trajectory E is configured at a greater angle than trajectory D. In an embodiment, the trajectory E is configured at an angle generally parallel to trajectory F.

The toe end height 192 of the walker 100 is measured between the horizontal ground and the anterior portion A and distal end Di of the outsole 102 when the strut supports 106 of the walker 100 are substantially perpendicular to the ground or parallel to axis X. The heel end height 190 is measured between the horizontal ground and the posterior portion P and distal end Di of the outsole 102 when the strut supports 106 of the walker 100 are substantially perpendicular to the ground or parallel to axis X. In a preferred embodiment, the struts support 106 are configured to follow the angle of the biomechanics of the lower limb. The angle of the biomechanics of the lower limb may be substantially perpendicular to the ground (e.g., approximately 88 degrees measured from a horizontally even surface) or parallel to axis X.

The peripheral edge 140 of the base 104 extends beyond the posterior end P of the outsole 102. In an embodiment, the peripheral edge 140 extends between 0.5 to 2.5 mm beyond the posterior end P of the outsole 102. In a preferred embodiment, the peripheral edge 140 extends 1.5 mm beyond the posterior end P of the outsole 102. The peripheral edge 140 may extend beyond the outsole 102 at other portions of the walker 100. By extending the peripheral edge 140 beyond the outsole 102, the overmold of the outsole 102 avoids a disadvantageous connection that would lead to inadvertent separation between the base 104 and the outsole 102. The base 104 may also feature a heel lip 122 that extends from the posterior end P of the posterior periphery 113.

Figures 6A, 6B, 7:
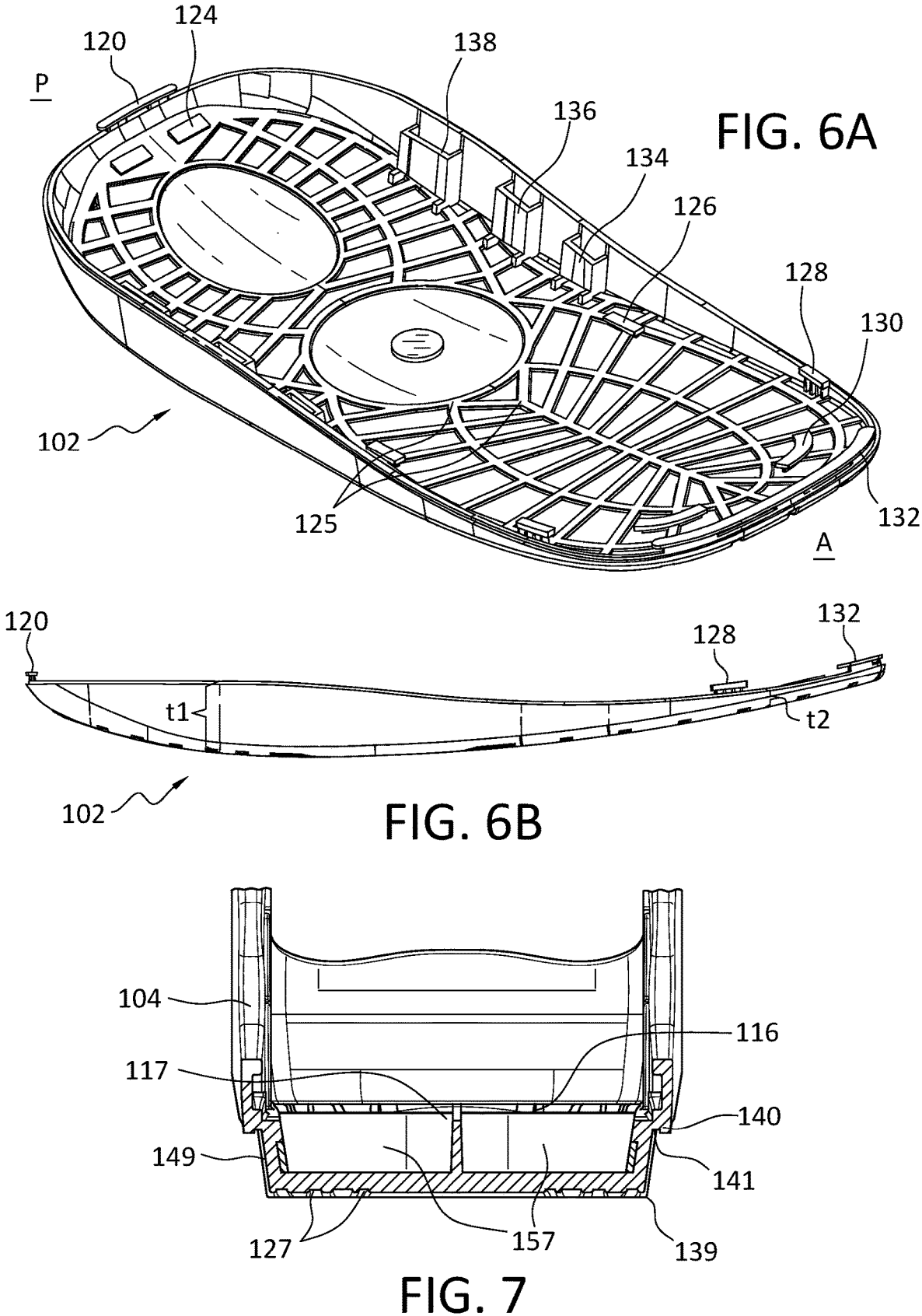
FIG. 6A is a perspective view of the outsole of FIG. 1.
FIG. 6B is a side plane view of the outsole of FIG. 1.
FIG. 7 is a cross-sectional front view of the base of the walker of FIG. 1.

FIG. 6A shows a top perspective view of the outsole 102 in FIG. 1. The outsole 102 comprises attachment posts 120, 124, 126, 128, 130, 132, 134, 136, and 138 that integrate with the base and can interlock therewith, preferably without an adhesive or glue; indeed, the base and outsole interlock so that the combined structure "consists" solely and only of the base and the outsole such that it is by the projections and recess of the base and outsole that interlock to secure retain each other. As the outsole may be overmolded onto the base, the outsole may be molded over the base, and due to its shrinkage forces, a shrink-fit is created between the outsole and the base such that the corresponding projections and recess securely and snugly interlock, thereby removing the necessity of an adhesive or glue. The outsole 102 comprises raised portions 125 that interface with recessed grooves 127 on the bottom of the base 104. The recessed grooves 127 of the base 104, as observed in FIG. 7, increase the connection and bonding to the outsole 102 by interfacing with the raised portions 125.

Nonetheless, the disclosure does not limit the outsole as only being applied to the base by overmolding, and an outsole and base may be secured to one another according to the disclosure with an adhesive or glue while possessing any of the features described herein.

FIG. 6B shows a side plane view of the outsole 102 in FIG. 1. Compared to conventional walkers, the heel thickness t1 of the overmolded outsole 102 is reduced to improve the user's gait and rollover of the walker. In one embodiment, the heel thickness t1 is less than 26 mm. In another embodiment, the heel thickness t1 is between 20 mm and 26 mm. The thickness t1 of the outsole 102 is reduced to more closely match the heel height of an unimpaired foot relative to the ground, whether in a shoe or without a shoe. The toe thickness t2 of the outsole 102 is less than the heel thickness t1. In an embodiment, the toe thickness t2 is determined by comparing the ratio of the heel end height 190 to the toe end height 192. In an embodiment, the heel end height of 190 to the toe end height of 192 is between 1.0 to 1.6 or between 1.15 to 1.45. In a preferred embodiment, the heel end height of 190 to the toe end of 192 is between 1.30 to 1.40, or approximately 1.35.

The toe thickness may be between 5 mm to 10 mm, wherein the toe thickness t2 of the base 104 is between 2 mm to 4 mm, and the toe thickness of the outsole 102 is between 3 mm to 6 mm. In an embodiment, the toe thickness t2 is 7.8 mm, wherein the toe thickness t2 of the base 104 is 3.26 mm, and the toe thickness of the outsole 102 is 4.57 mm. The ratio measurements for heel thickness t1 and toe thickness t2 are measured with the walker 100 standing by itself on an even horizontal surface wherein the strut follows the angle of the lower limb biomechanics.

FIG. 7 shows a cross-sectional front view of the base 104 of the walker of FIG. 1. The base 104 features sunken grooves 127 to receive and integrate with the overmolded outsole 102. The base 104 forms an inner peripheral edge 139 that interfaces with the overmolded outsole 102. The base 104 comprises a lower peripheral edge 149. The lower peripheral edge 149 may be textured to increase the connection between the base 104 and the overmolded outsole 102. The base 104 features a groove 141 within the peripheral edge 140 of the base 104 to receive the overmolded outsole 102 for the shrink-fit. The groove 141 follows the peripheral edge 140 of the base 104 around the walker 100 and avoids detachment of the outsole 102 from the sides SI, SII of the base 104.

Due to manufacturing limitations, traditional walker bases have featured holes or openings on the sides of the base about the ankle supporting sections. The base 104 in FIG. 7 is devoid of the traditionally featured holes and is continuously formed around the lower peripheral edge 149. The lower peripheral edge 149 surrounds the heel lattice structure 117 and creates hollow spaces 157 within the heel support 116 of the base 104. The base 104 is thus lighter than traditional walker bases and provides a greater surface area around the lower peripheral edge 149 to mate with the outsole 102.

Of course, while a preferred embodiment involves overmolding the outsole to the base, the protrusions and recesses or similarly defined structure, can interlock without molding such that the protrusions and recesses are sized and configured for interlocking after molding, and a suitable adhesive may be used to maintain them in place, although they may be sized and configured to press-fit without an adhesive. Moreover, the illustrated and described protrusions and recesses are not limited to those shown and described, and suitable corresponding protrusions and recesses may be provided in different locations, sizes and shapes on either the outsole or base.

FIG. 8 shows a bottom plane view of the base 104. The base 104 includes openings or recesses 142, 144, 146, 148, 150, 152, 154, 156, 158 through which the material of the outsole 102 extends to unite the base 104 and the outsole 102, forming the aforementioned interlocking due to a shrink-fit. The outer heel openings 142 receive the outer heel attachment post 120. The inner heel openings 144 receive the inner heel attachment posts 124. The side attachment openings 146 receive the attachment posts 126. The front edge openings 148 receive the front edge attachment posts 128. The inner toe openings 150 receive the inner toe attachment posts 130. The outer toe openings 152 receive the outer toe attachment post 132. The front, middle, and back side openings 154, 156, and 158 receive the front, middle, and back side attachment posts 134, 136, and 138, respectively.

Figure 9:
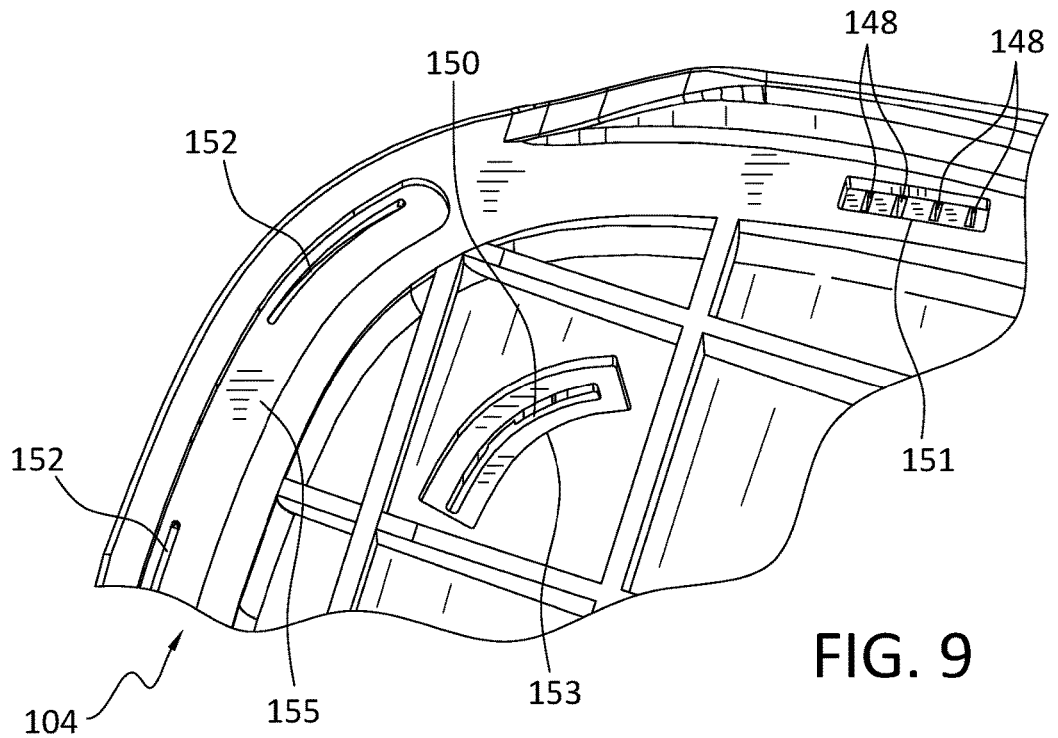
FIG. 9 is a sectional perspective view of the top of the base of the walker in FIG. 1.

FIG. 9 shows a sectional perspective view of the top of the base 104. The material properties of the overmolded outsole 102 allow for attachment posts 132 and 128 to receive a material of the outsole 102 through multiple openings 148 and 152 into channels 151 and 155, respectively. The material of attachment post 130 extends through single opening 150 into channel 153. It is preferred that the outsole 102 extends through multiple outer toe openings 152 and forms a single outer toe attachment post 132 to withstand frontal impact during walking. It is also preferred that the outsole 102 extends through multiple outer heel openings 142 and forms a single outer heel attachment post 120 to withstand rear impact during walking.

Figure 10:
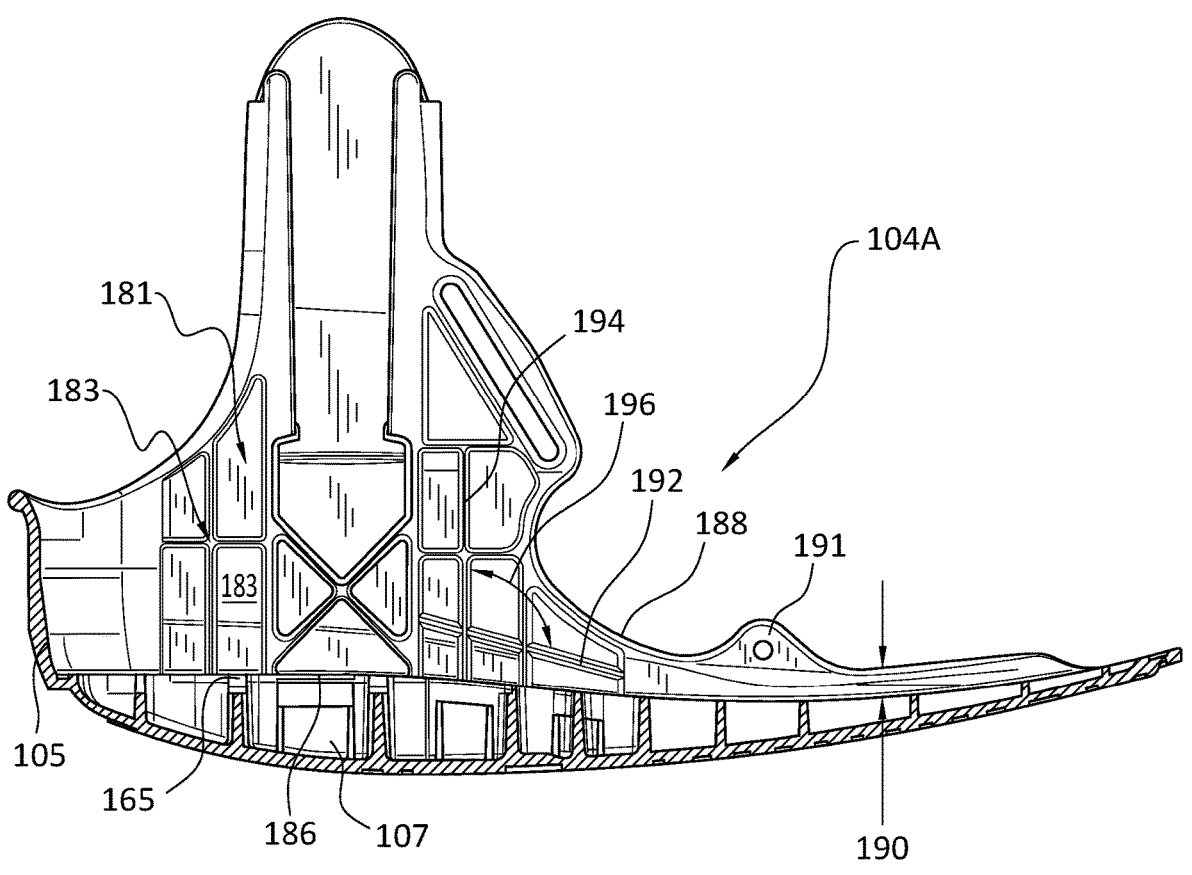
FIG. 10 is a cross-sectional view of a variation of the base of the walker in FIG. 3A.

FIG. 10 illustrates another variation of the base 104A of the walker. The side wall 181 may have a grid-structure 183 (similar to the lattice structure mentioned above, with preferably shallower ribs) to reinforce the side wall 181. The grid-structure 183 involves a plurality of ribs 192, 194, defining a plurality of recesses 183 between the ribs 192, 194. The recesses 183 reduce the side wall's material without significantly adding weight since the strength is borne by the ribs (where a localized thickness is achieved). According to the embodiment of FIG. 10, while conventionally it is understood to provide a linear grid-structure such that generally the ribs are arranged at 90 degrees relative to one another, the embodiment unexpectedly finds that by making a lateral rib 192 arranged obliquely at an oblique angle 196 relative to a longitudinal rib(s) 194 (the lateral rib 192 may cross multiple longitudinal ribs), the strength of the side wall may be enhanced. Moreover, the oblique angle may generally correspond to the orientation of the upper peripheral edge 188 along the footbed of the walker base.

FIG. 10 illustrates that the walker may be arranged with a pivot point 191 for receiving a pivotable D-ring, as in U.S. Pat. No. 7,896,826. Moreover, FIG. 10 illustrates how the upper peripheral edge 188 is located at a thickness 190 from the inner contour, such that the thickness is at least the thickness of the insole such that the insole does not preferably protrude above the upper peripheral edge 188.

By providing an orthopedic walker according to the embodiments of the disclosure, an orthopedic walker may combine the benefits of an existing orthopedic brace in a walker that is both lightweight compared to existing devices and nevertheless comprises necessary strength and rigidity for immobilization and support of a limb of a user.

It is to be understood that not necessarily all objects or advantages may be achieved under an embodiment of the disclosure. Those skilled in the art will recognize that an orthopedic walker may be embodied or carried out. Hence, it achieves or optimizes one advantage or group of advantages as taught herein without achieving other objects or advantages as taught or suggested herein.

A skilled artisan will recognize the interchangeability of various disclosed features. Other known equivalents for each feature can be mixed and matched by one of ordinary skill in this art to build and use an orthopedic device under the principles of the present disclosure. The skilled artisan will understand that the features described may be adapted to other methods and types of orthopedic and prosthetic devices.

Although this disclosure describes certain exemplary embodiments and examples of an orthopedic walker, it will be understood by those skilled in the art that the present disclosure extends beyond the specifically disclosed structure to alternative embodiments and/or uses of the disclosure and obvious modifications and equivalents thereof, including other types and components of orthopedic, prosthetic, and medical devices. It is intended that the present disclosure should not be limited by the disclosed embodiments described above and may be extended to other applications that may employ the features described.

The invention claimed is:

1. An orthopedic walker, comprising:
a base including two strut supports, a heel support, and a toe support; and
an outsole overmolded to the base at the heel support and the toe support;
wherein the outsole is formed from a plastic material and has protrusions or recesses interlocking corresponding protrusions or recesses of the base, the outsole is secured attached in place to the base due to a shrink-fit about at least a portion of the base and without an adhesive;
wherein the heel support comprises a heel lattice structure is constructed of at least one rib extending between sides of the walker, the at least one rib tapering in thickness toward a median plane of the walker.

2. The orthopedic walker of claim 1, wherein the heel lattice structure comprises at least one medial rib that extends parallel to a median plane of the walker.

3. The orthopedic walker of claim 1, wherein the base forms a peripheral edge that extends past the outsole at a posterior portion of the walker.

4. The orthopedic walker of claim 1, wherein the base is provided with a groove at a distal end of the base to interface with and secure the outsole within a peripheral edge of the base.

5. The orthopedic walker of claim 1, wherein an anterior periphery of the base forms a transition at a toe end.

6. The orthopedic walker of claim 1, wherein the base and the outsole curve upward toward an anterior portion of the walker.

7. The orthopedic walker of claim 1, wherein the base is provided with reinforcements along the strut supports to restrict movement.

8. The orthopedic walker of claim 1, wherein the base is designed with a lip on the heel to aid in donning and doffing the walker.

9. The orthopedic walker of claim 1, wherein a peripheral edge of the base extends past the outsole.

10. The orthopedic walker of claim 1, wherein an internal peripheral edge of the base sits flush against an inside surface of the outsole.

11. The orthopedic walker of claim 1, wherein the outsole has a thickness at the heel and continues in an upward curve, becoming thinner until it reaches a thickness at the toe support.

12. The orthopedic walker of claim 1, wherein a heel plate is inserted into the base, the base having a plurality of seat tabs retaining the heel plate below an inner contour of the base along which an insole may be arranged for placement in the base.

13. An orthopedic walker, comprising:

a base including two strut supports, a heel support, and a toe support, wherein the heel support comprises a heel lattice structure is constructed of at least one rib extending between sides of the walker;

an outsole overmolded to the base at the heel support and the toe support;

a heel plate extending over the heel lattice structure; and an insole placed over the heel plate and extends from the heel support to the toe support;

wherein the outsole is formed from a thermoplastic elastomer and has protrusions or recesses interlocking corresponding protrusions or recesses of the base maintained in place due to a shrink-fit about at least a portion of the base, the base being formed from a structural plastic including a filled polymer;

wherein the at least one rib tapers in thickness toward a median plane of the walker.

14. The orthopedic walker of claim 13, wherein the heel lattice structure comprises at least one medial rib that extends parallel to a median plane of the walker.

15. The orthopedic walker of claim 13, wherein the base has a plurality of seat tabs retaining the heel plate below an inner contour of the base along which the insole is arranged for placement in the base.

* * * * *